(12) United States Patent
Hunter et al.

(10) Patent No.: US 12,729,945 B2
(45) Date of Patent: Sep. 8, 2026

(54) DEVICES AND METHODS FOR A RETAINER ADAPTER ASSEMBLY

(71) Applicant: Regeneron Pharmaceuticals, Inc., Tarrytown, NY (US)

(72) Inventors: Christopher Hunter, Castleton-on-Hudson, NY (US); Connor Block, Troy, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 345 days.

(21) Appl. No.: 18/178,026

(22) Filed: Mar. 3, 2023

(65) Prior Publication Data

US 2023/0280148 A1 Sep. 7, 2023

Related U.S. Application Data

(60) Provisional application No. 63/316,814, filed on Mar. 4, 2022.

(51) Int. Cl.
*G01B 5/252* (2006.01)
*A61M 5/178* (2006.01)

(52) U.S. Cl.
CPC ............ *G01B 5/252* (2013.01); *A61M 5/178* (2013.01); *A61M 2205/70* (2013.01)

(58) Field of Classification Search
None
See application file for complete search history.

(56) References Cited

U.S. PATENT DOCUMENTS 3,702,608 A * 11/1972 Tibbs .................... A61M 5/422 604/136
4,826,491 A * 5/1989 Schramm ........... A61M 5/3243 604/263
4,923,447 A * 5/1990 Morgan ............. A61M 5/3271 604/263
D319,573 S 9/1991 Rogers
D333,184 S 2/1993 Taylor
D334,620 S 4/1993 Taylor
5,417,660 A * 5/1995 Martin ................ A61M 5/3271 604/110

(Continued)

FOREIGN PATENT DOCUMENTS

KR 20170074969 A 6/2017

OTHER PUBLICATIONS

International Search Report for International Application No. PCT/US2023/063693, dated Jun. 7, 2023 (3 pages).

*Primary Examiner* — Mark A Shabman
(74) *Attorney, Agent, or Firm* — Bookoff McAndrews, PLLC

(57) ABSTRACT

An adapter assembly that includes a housing, a channel formed within the housing that is configured to receive a medical device, a first groove formed along an interior wall of the channel that is configured to at least partially receive a first retaining element, and a second groove formed along the interior wall of the channel that is configured to at least partially receive a second retaining element. The first retaining element is configured to extend outward from the first groove and the second retaining element is configured to extend outward from the second groove, such that the first and second retaining elements abut against the medical device received through the channel.

20 Claims, 7 Drawing Sheets

(56) References Cited

U.S. PATENT DOCUMENTS 5,681,292 A * 10/1997 Tober .................. A61M 5/3234 604/110
D423,917 S 5/2000 Remmers et al.
6,193,695 B1 * 2/2001 Rippstein, Jr. ...... A61M 5/3234 604/110
6,319,233 B1 * 11/2001 Jansen .................. A61M 5/326 604/192
6,610,076 B2 8/2003 Hellenkamp
D502,773 S 3/2005 Abry
6,941,947 B2 9/2005 Young et al.
D548,833 S 8/2007 Young et al.
7,300,416 B2 * 11/2007 Botich .................... A61M 5/24 604/110
D556,904 S 12/2007 Clarke
D559,388 S 1/2008 Melcher
D583,053 S 12/2008 Zhukauskas et al.
7,553,293 B2 * 6/2009 Jensen .................. A61M 5/326 604/110
D613,849 S 4/2010 Smutney et al.
D619,705 S 7/2010 Foy et al.
D652,933 S 1/2012 Boschetti Sacco
D664,640 S 7/2012 Smutney et al.
8,647,299 B2 2/2014 Stamp
D723,679 S 3/2015 Neff et al.
9,579,468 B2 * 2/2017 Schoonmaker ..... A61M 5/3257
D789,540 S 6/2017 Gyorgy
D863,574 S 10/2019 Yan et al.
D865,997 S 11/2019 Mellett et al.
D896,971 S 9/2020 Held et al.
D906,516 S 12/2020 Uridil et al.
D913,483 S 3/2021 Boschetti Sacco
D916,306 S 4/2021 Du
D925,033 S 7/2021 Uridil et al.
D940,313 S 1/2022 Heine et al.
D941,120 S 1/2022 Switzer
D953,847 S 6/2022 Blair et al.
D968,593 S 11/2022 Tamir et al.
D988,123 S 6/2023 Robillard et al.
D1,007,677 S 12/2023 Zhao et al.
D1,023,331 S 4/2024 Wu
D1,024,321 S 4/2024 Hunter et al.
D1,028,224 S 5/2024 Hunter et al.
D1,043,968 S 9/2024 Stetsko et al.
D1,057,944 S 1/2025 Hunter et al.
D1,099,307 S 10/2025 Kolenda
D1,104,279 S 12/2025 Xie
2003/0183545 A1 * 10/2003 Lauryssen .............. A61B 5/153 604/181
2004/0111063 A1 * 6/2004 Botich .................. A61M 5/286 604/110
2010/0152655 A1 * 6/2010 Stamp ..................... A61M 5/24 604/196
2015/0335825 A1 11/2015 Soerensen
2019/0350466 A1 11/2019 Boschetti Sacco
2023/0280148 A1 9/2023 Hunter et al.

* cited by examiner

DEVICES AND METHODS FOR A RETAINER ADAPTER ASSEMBLY

CROSS-REFERENCE TO RELATED APPLICATION

This application claims the benefit of priority from U.S. Provisional Patent Application No. 63/316,814, filed Mar. 4, 2022, the entirety of which is incorporated by reference herein.

FIELD OF THE DISCLOSURE

Aspects of the present disclosure relate to devices and methods for positioning, controlling, and retaining a medical device during testing procedures. More specifically, embodiments of the present disclosure relate to devices and methods for holding, suspending, aligning, and/or maintaining a position of a medical device (e.g., a syringe) relative to instrumentation for testing various characteristics of the medical device

INTRODUCTION

Medical devices for storing drug products, such as syringes storing fluid substances, may be required to undergo various testing procedures to ensure proper and safe functionality. Testing instruments may be utilized to facilitate such testing, including, but not limited to, compressive and tensile tests. In some instances, a load (e.g., a force) may be inadvertently applied to the syringe by the testing instrumentation and/or other devices (e.g., during setup), thereby causing inaccuracies in the test results, or premature failures. In other instances, human error in handling, controlling, or positioning the syringe relative to the testing instrumentation prior to administering the test may similarly impact the results.

The application of an inadvertent load to a syringe prior to administering a test (referred to herein as "pre-load") may cause additional complications for automating a testing process of the syringe. For example, occurrences of a pre-load to the syringe may result in a misalignment of the syringe relative to a testing site and/or the testing instrument, thereby causing results or specimen damage during the testing process.

SUMMARY

Disclosed herein are adapter assemblies, and particularly adapters for attaching, holding, aligning, and/or controlling a position and/or orientation of a syringe relative to testing instrumentation and/or a testing site. In one embodiment of the present disclosure, an adapter assembly includes a housing including a channel formed within the housing. The channel is defined by a pair of openings positioned on opposing surfaces of the housing, and configured to at least partially receive a portion of a medical device, e g, a barrel portion of a syringe body. The adapter assembly includes a first groove, formed along an interior wall of the channel, that is configured to at least partially receive a first retaining element. The adapter assembly may include a second groove, formed along the interior wall of the channel, that is configured to at least partially receive a second retaining element. The first retaining element is configured to extend outward from the first groove (e.g., radially-inward relative to the interior wall) and the second retaining element is configured to extend outward from the second groove (e.g., radially-inward relative to the interior wall), such that each of the first retaining element and the second retaining element abut against (and make contact with) a body of the medical device received through the channel. The first retaining element and the second retaining element are configured to align the body of the medical device relative to a central longitudinal axis of the channel, and to offset a proximal end of the medical device from the housing.

BRIEF DESCRIPTION OF THE DRAWINGS

The accompanying drawings, which are incorporated into and constitute a part of this specification, illustrate various exemplary embodiments and, together with the description, serve to explain principles of the disclosed embodiments. The drawings show different aspects of the present disclosure and, where appropriate, reference numerals illustrating like structures, components, materials, and/or elements in different figures are labeled similarly. It is understood that various combinations of the structures, components, and/or elements in various embodiments, other than those specifically shown, are contemplated and are within the scope of the present disclosure.

Figure 1:
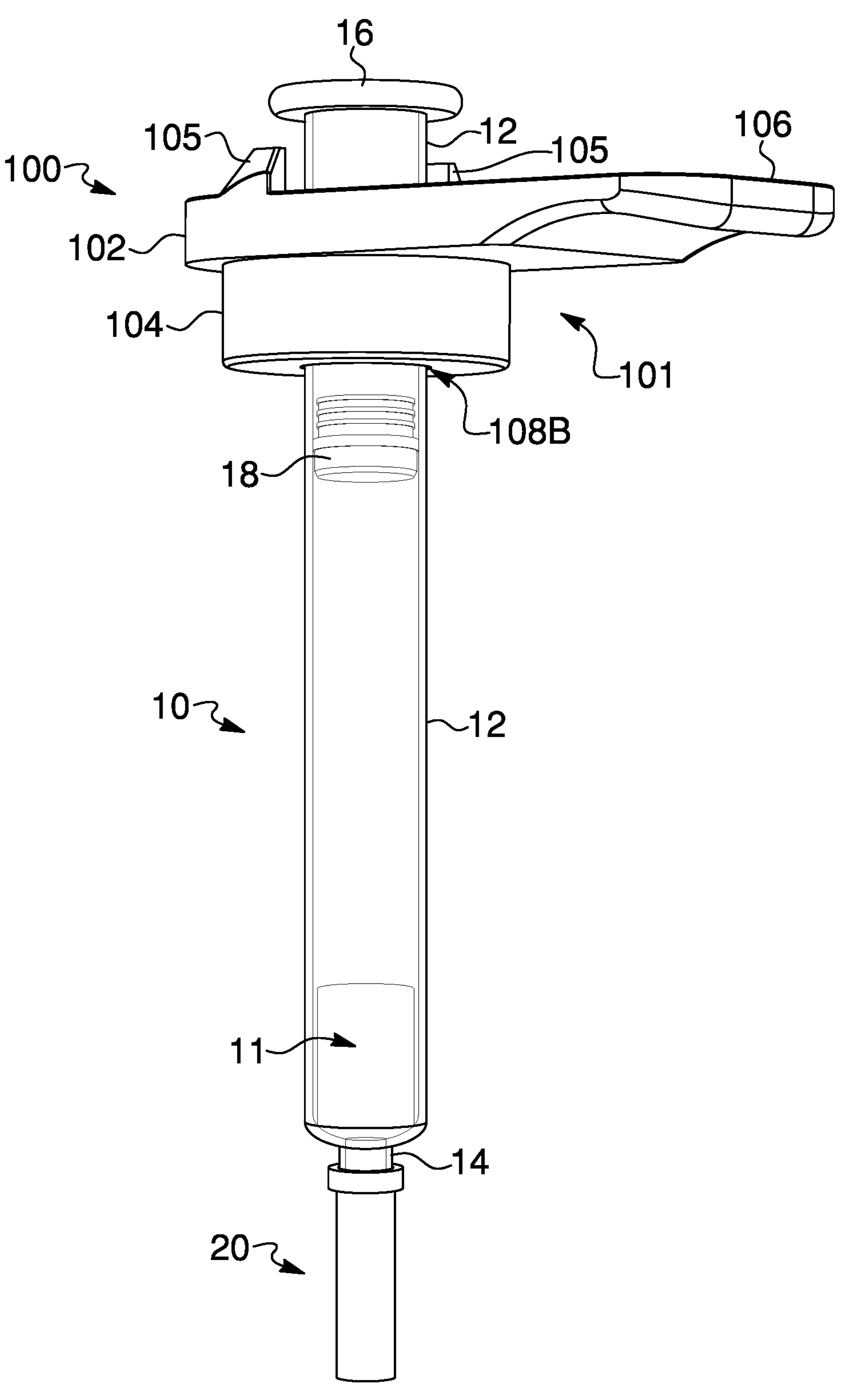
FIG. 1 depicts a perspective view of an exemplary adapter assembly receiving an example syringe barrel therein, according to aspects of the present disclosure.

There are many embodiments described and illustrated herein. The present disclosure is neither limited to any single aspect nor embodiment thereof, nor to any combinations and/or permutations of such aspects and/or embodiments. Each of the aspects of the present disclosure, and/or embodiments thereof, may be employed alone or in combination with one or more of the other aspects of the present disclosure and/or embodiments thereof. For the sake of brevity, many of those combinations and permutations are not discussed separately herein.

DETAILED DESCRIPTION

As used herein, the terms "comprises," "comprising," "includes," "including," or any other variation thereof, are intended to cover a non-exclusive inclusion, such that a process, method, article, or apparatus that comprises a list of elements does not include only those elements, but may include other elements not expressly listed or inherent to such process, method, article, or apparatus. The term "exemplary" is used in the sense of "example," rather than "ideal." Notably, an embodiment or implementation described herein as an "example" or "exemplary" is not to be construed as preferred or advantageous, for example, over other embodiments or implementations; rather, it is intended reflect or indicate the embodiment(s) is/are one "example," rather than "ideal." In addition, the terms "first," "second" and the like, herein do not denote any order, quantity, or importance, but rather are used to distinguish an element, a structure, a step or a process from another. Moreover, the terms "a" and "an" herein do not denote a limitation of quantity, but rather denote the presence of one or more of the referenced items. Additionally, the terms "about," "approximately," "substantially," and the like, when used in describing a numerical value, denote a variation of +/−10% of that value, unless specified otherwise.

Embodiments of the present disclosure may be used with any type of fluid-containing products, such as liquid drug substances, liquid placebos, or other liquids (or liquid solutions) that may be dispensed in a dose form. As used herein, the term "substance" may refer to a formulated substance including an active ingredient or ingredients. In some embodiments, devices and aspects of the present disclosure can be used with any therapies using the immune system to combat diseases, such as immunotherapies, including vaccines, allergy treatments, cancer treatments, and more. In particular, devices and aspects of the present disclosure can be used for the treatment of patients with cancer (e.g., immune-oncology). However, it is also contemplated that embodiments of the present disclosure may be applicable to any therapy, liquid products, and/or any other context for which different substances may be stored separately in multiple vials. While medical indications are described herein, it is contemplated that non-medical liquids packaged together in different vials may be used in conjunction with the vial adapters described herein. It should be understood that embodiments of the present disclosure may be used with fluid-containing products (e.g., syringes) that are empty and do not contain any liquid substances, such as for component qualification purposes.

As used herein, the terms "proximal" and "proximally" refer to a location (or portion of a device) relatively closer to, or in the direction of, a user end opposite a distal location/portion of a device, and the terms "distal" and "distally" refer to a location (or portion of a device) relatively closer to, or in the direction of, an access point. As used herein, the term "body," when used in reference to a part of a device, may refer to a component of the device suitable for containing a volume of a drug substance. A body may include, e.g., a barrel (such as a syringe barrel), tube, cylinder, or other containing portion of a device. In some embodiments, a body may also include a distal end portion having a nozzle, needle, needle attachment site, and/or distal cap.

Described herein are various embodiments of adapter assemblies, and in particular, for holding a syringe relative to an instrument or device for testing certain characteristics of the syringe. In some instances, embodiments or aspects of embodiments disclosed herein may be used in conjunction with syringes of various shapes and/or sizes. In other instances, embodiments or aspects of embodiments disclosed herein may be used with other types of fluid-containing products, including, but not limited to, vials, cartridges, and/or other suitable medical devices. Such adapter assemblies may be intended to reduce human error and/or increase accuracy of administering a test of the characteristics or functionality of the medical device.

Referring now to FIG. 1, an exemplary adapter assembly 100 is depicted. Adapter assembly 100 may be configured and operable to retain and suspend a medical device relative to a testing instrument or testing site. Adapter assembly 100 may include a housing 101 defined by a proximal body 102 and a distal body 104. Proximal body 102 may have a greater cross-sectional profile than distal body 104. As described herein, each of proximal body 102 and distal body 104 may be sized, shaped, and configured to form a frictional fit with a corresponding portion of a testing instrument. Housing 101 may include a handle 106 extending laterally outward from proximal body 102. Handle 106 may have an ergonomic profile that is configured to facilitate a user in manually manipulating housing 101, such as to insert and/or remove adapter assembly 100 to/from a testing instrument.

Housing 101 may include opposing outer surfaces, such as at a proximal (top) surface of proximal body 102 and at a distal (bottom) surface of distal body 104. Adapter assembly 100 may include one or more alignment mechanisms 105 positioned on housing 101. In the example, adapter assembly 100 may include at least a pair of alignment mechanisms 105 extending proximally from the proximal (top) surface of proximal body 102. The pair of alignment mechanisms 105 may be configured to facilitate a positioning, an alignment, and/or an orientation of a medical device relative to adapter assembly 100, and particularly the proximal (top) surface of proximal body 102. As described herein, alignment mechanisms 105 may serve as a visual reference points for positioning the medical device that is coupled to adapter assembly 100.

As seen in FIG. 1, the medical device may include a syringe 10 having a body 12 for storing a substance 11. Body 12 may have a longitudinal length defined between a distal end 14 and a proximal end 16, with a stopper 18 (e.g., a plunger) disposed within a cavity of body 12. In some embodiments, syringe 10 may omit substance 11 and/or exclude stopper 18. Syringe 10 may include a needle 15 (see FIG. 5) extending distally from distal end 14. Needle 15 may be in fluid communication with the cavity of body 12, including the substance 11 stored within body 12. In some examples, syringe 10 may include a removable cap 20 (e.g., a rigid needle shield or a soft needle shield) selectively coupled to distal end 14 for covering needle 15 when syringe 10 is not in use. In other examples, cap 20 may be omitted entirely. It should be appreciated that various other suitable medical devices may be used in conjunction with adapter assembly 100.

Proximal end 16 may define a flange of syringe 10, such that the pair of alignment mechanisms 105 may be configured to facilitate a position of the flange relative to the proximal (top) surface of proximal body 102. In the embodiment, the pair of alignment mechanisms 105 may include projections defining a visual sight for inspection and reference by a user of adapter assembly 100, such as when coupling syringe 10 to housing 101. For example, a user may determine a desired position of body 12 relative to housing 101 in reference to a corresponding distance between the flange at proximal end 16 to the pair of alignment mechanisms 105.

Although a pair of alignment mechanisms 105 are shown and described herein, adapter assembly 100 may include additional and/or fewer alignment mechanisms 105 without departing from a scope of this disclosure. Additionally and/or alternatively, alignment mechanisms 105 may be positioned along various other surfaces and/or walls of housing 101 than the proximal (top) surface of proximal body 102. It should be appreciated that alignment mechanisms 105 may have various other suitable sizes, shapes, and/or configurations than those shown and described herein.

Figure 2:
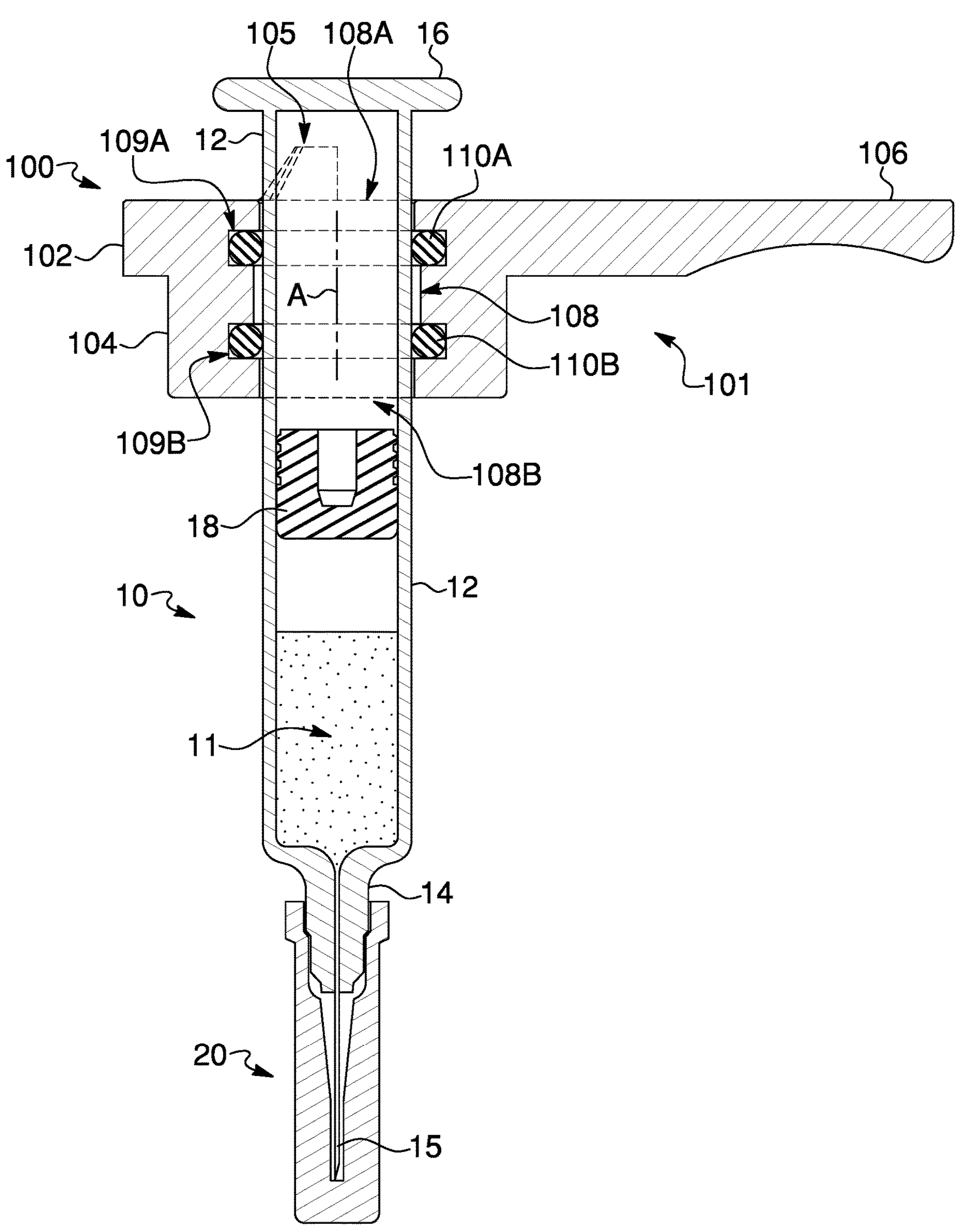
FIG. 2 depicts a cross-sectional side view of the adapter assembly and the syringe depicted in FIG. 1, according to aspects of the present disclosure.

Referring to FIG. 2, adapter assembly 100 may include a channel 108 extending through housing 101, and particularly through each of proximal body 102 and distal body 104. Channel 108 may have a longitudinal length defined between opposing outer surfaces of housing 101, such as the proximal (top) surface of proximal body 102 and the distal (bottom) surface of distal body 104. Housing 101 may include a first opening 108A along the proximal (top) surface of proximal body 102, and a second opening 108B along the distal (bottom) surface of distal body 104. Channel 108 may extend between first opening 108A and second opening 108B, and may be configured to receive syringe 10 through housing 101 via first opening 108A and second opening 108B. Channel 108 may have a generally uniform cross-sectional configuration. In some embodiments, one portion of channel 108 may have a cross-sectional configuration that differs from another portion of channel 108.

Housing 101 may further include one or more slots and/or grooves formed within channel 108, such as along an interior wall defining channel 108. Each of the one or more grooves may be sized and shaped to receive a retaining element. In the example, housing 101 may include a first groove 109A and a second groove 109B. First groove 109A may be positioned adjacent to the proximal (top) surface of proximal body 102 relative to second groove 109B, and second groove 109B may be positioned adjacent to the distal (bottom) surface of distal body 104 relative to first groove 109A.

Still referring to FIG. 2, each of first groove 109A and second groove 109B may extend about an interior wall and/or surface defining channel 108, such that each groove may have a length that is transverse (e.g. perpendicular) to a central longitudinal axis A of channel 108. First groove 109A and second groove 109B may be positioned about a perimeter of body 12 when syringe 10 is received within channel 108. First and second grooves 109A, 109B may extend entirely around the periphery of channel 108 or only a portion thereof. Moreover, portions of first and second grooves 109A, 1098 may overlap one another, whereas other portions of first and second grooves 109A, 109B may not overlap one another. Still further, although the present disclosure depicts that first and second grooves 109A, 109B extend in planes substantially perpendicular to the central longitudinal axis A of channel 108, those of ordinary skill in the art will readily recognize that such grooves may extend in planes parallel to the central longitudinal axis A. Furthermore, although FIG. 2 depicts two circumferential grooves 109A, 109B, more or less grooves may be provided according to the principles of the present disclosure.

First groove 109A may be configured to receive a first retaining element 110A, and second groove 109B may be configured to receive a second retaining element 110B, First and second retaining elements 110A, 110B may extend entirely around the periphery of channel 108 or only a portion thereof, in accordance with a corresponding configuration of the respective grooves. Moreover, portions of first and second retaining elements 110A, 110B may overlap one another, whereas other portions of first and second retaining element 110A, 110B may not overlap one another. Although the present disclosure depicts first and second retaining elements 110A, 110B extending in planes substantially perpendicular to the central longitudinal axis A, those of ordinary skill in the art will recognize that such retaining elements may extend in planes parallel to the central longitudinal axis A. Although only two circumferential retaining elements 110A, 110B are shown and described herein, it should be appreciated that additional and/or fewer retaining elements may be provided in accordance with a corresponding number of grooves.

Figure 3:
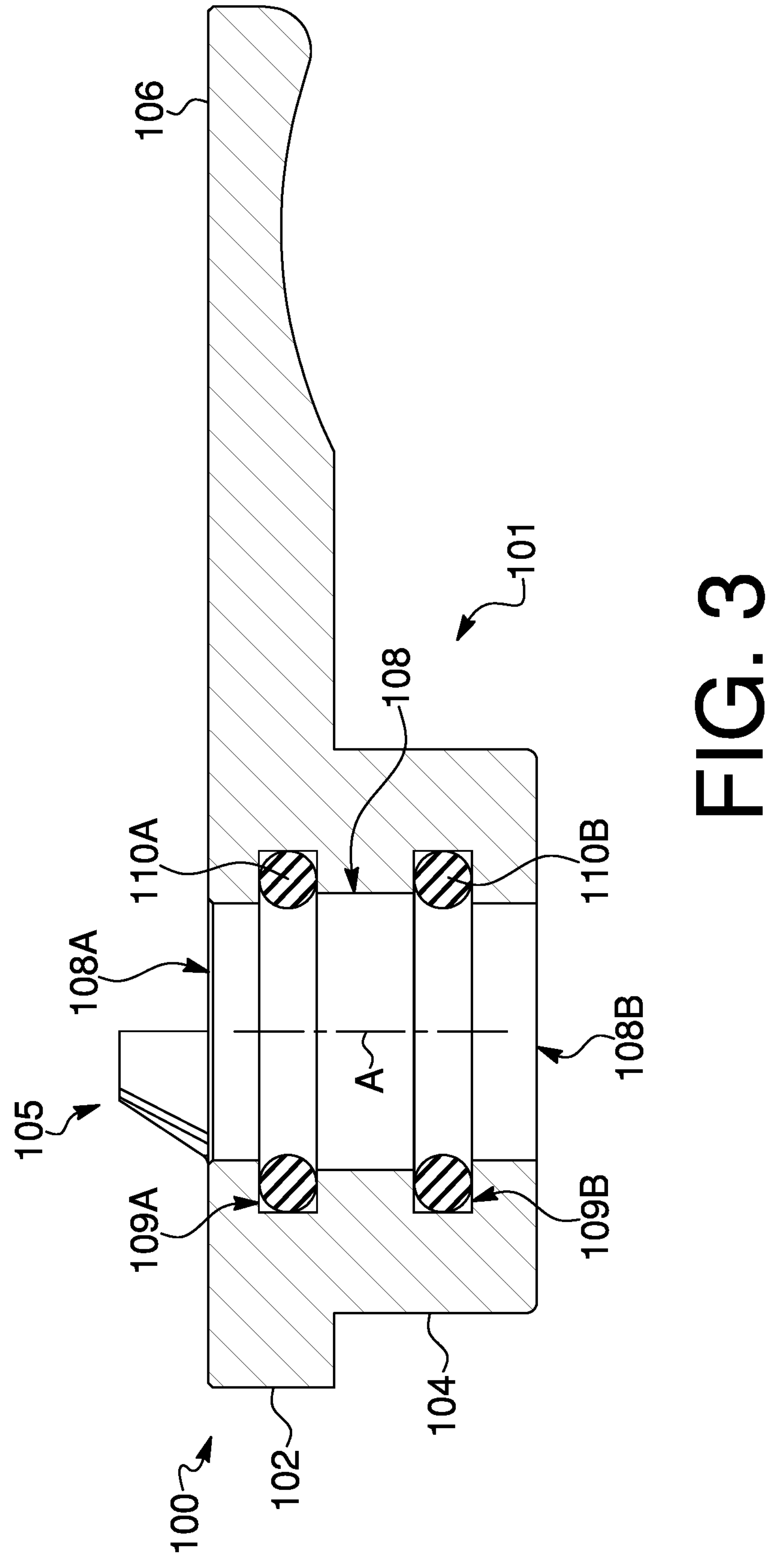
FIG. 3 depicts a cross-sectional side view of the adapter assembly of FIG. 1, according to aspects of the present disclosure.

As best seen in FIG. 3, each of first retaining element 110A and second retaining element 110B may be sized and/or shaped to extend at least partially outward from the corresponding groove. Stated differently, retaining elements 110A, 110B may extend radially-inward from and/or relative to the interior wall of housing 101, Accordingly, first retaining element 110A and second retaining element 110B may extend into channel 108 and toward the central longitudinal axis A. In some embodiments, one or more of first groove 109A and second groove 109B may be oversized to allow greater clearance and/or space for the respective retaining element to flex therein.

As described below, first retaining element 110A and second retaining element 110B may be configured to contact an outer surface of body 12 when syringe 10 is received through channel 108. First retaining element 110A and second retaining element 110B may be configured to retain syringe 10 in a fixed position, orientation, and/or alignment relative to housing 101 and a testing site upon engaging body 12 within channel 108.

First groove 109A and second groove 1098 may be longitudinally spaced apart from one another (in a direction parallel to the central longitudinal axis A of channel 108) by a minimum predetermined distance to facilitate an optimal retention of syringe 10 relative to housing 101. Stated differently, an offset between first groove 109A and second groove 109B, and the corresponding separation between the retaining elements received in each, may be configured to improve an engagement between housing 101 and syringe 10. Further, an offset distance between first groove 109A and second groove 109B may improve an alignment of body 12 within channel 108, such as relative to the central longitudinal axis A, when syringe 10 is received through housing 101. As described herein, adapter assembly 100 may be configured to suspend (e.g., hold) syringe 10 within housing 101 and align needle 15 or needle shield 20 relative to a testing site. In some embodiments, syringe 10 may omit needle shield 20 entirely such that needle 15 may be exposed at distal end 14. Adapter assembly 100, via retaining elements 110A, 110B, may be configured to retain syringe 10 therein until a suitable force is applied to syringe 10.

Still referring to FIG. 3, a relative position of first groove 109A and second groove 109B define two concentric points of contact for adapter assembly 100. Although a pair of grooves and a corresponding pair of retaining elements are shown and described herein, it should be appreciated that additional and/or fewer grooves and retaining elements may be included in adapter assembly 100 without departing from a scope of this disclosure. A cross-sectional dimension of channel 108, first retaining element 110A, and/or second retaining element 110B may at least partially define a grip diameter of adapter assembly 100.

In some embodiments, first groove 109A and second groove 109B may have a similar size and/or shape, while in other embodiments the grooves may have varying sizes and/or shapes relative to one another. Similarly, first retaining element 110A and second retaining element 110B may have similar or varying sizes and/or shapes relative to one another. A material composition of retaining elements 110A, 110B may further adjust the grip diameter of adapter assembly 100, such as based on a relative elasticity and/or flexibility of the material. Accordingly, the grip diameter of adapter assembly 100 may be substantially constant and/or may vary along the central longitudinal axis A of channel 108.

In one example, first retaining element 110A and second retaining element 110B may be formed of an elastomeric material that is flexibly deformable. Accordingly, the pair of retaining elements 110A, 110B may be configured to flex and/or deform when syringe 10 is received through channel 108, thereby applying a radially-inward force against body 12 to retain syringe 10 within housing 101.

In some examples, the retaining elements 110A, 110B may include rubber O-rings formed of Viton® with a shore hardness ranging from about 80 A to about 90 A, such as 85 A. In other examples, the retaining elements 110A, 110B may include various suitable seals, gaskets, inserts, and other similar devices. Those of ordinary skill in the art will readily recognize that retaining elements 110A, 110B may be made of any suitable material, such as, e.g., rubber or suitable fluoroelastomers. Housing 101, including proximal body 102, distal body 104, and handle 106, may be formed of various materials, such as carbon fiber nylon, polyetheretherketone (PEEK) carbon fiber, and other similar materials.

In exemplary use, adapter assembly 100 may be operable to facilitate testing of a medical device, such as syringe 10, with a testing instrument. It should be appreciated that adapter assembly 100 may facilitate testing of syringe 10 with or without a substance 11 or stopper 18 disposed within body 12, and/or needle shield 20 coupled to needle 15. Syringe 10 (or other medical device) may be coupled to adapter assembly 100 by inserting body 12 through channel 108, as shown in FIG. 1. First retaining element 110A and second retaining element 110B may interface with an exterior of body 12 as syringe 10 is received in first opening 108A, through channel 108, and out of housing 101 from second opening 108B.

First retaining element 110A and second retaining element 110B may be configured to flex upon engaging with body 12. In particular, the pair of retaining elements 110A, 110B may compress radially-outward (e.g., away from the central longitudinal axis A of channel 108) when body 12 is received through channel 108, thereby forming a frictional fit against an exterior of syringe 10 (see FIG. 2). The frictional fit may be configured to retain syringe 10 within adapter assembly 100 until a suitable force is applied to syringe 10, as described in more detail below. First retaining element 110A and second retaining element 110B may be configured to automatically align syringe 10 with the central longitudinal axis A as syringe 10 is inserted through housing 101. As described herein, by aligning syringe 10 within channel 108, adapter assembly 100 may be configured to improve an alignment of needle 15 and/or needle shield 20 relative to a testing site when the assembly of syringe 10 and adapter assembly 100 is coupled to a testing instrument (see FIGS. 4-5).

It should be appreciated that syringe 10 may be movable relative to housing 101 despite the pair of retaining elements 110A, 110B engaging body 12 within channel 108, such that a user of adapter assembly 100 may position syringe 10 at a desired depth relative to housing 101. First retaining element 110A and second retaining element 110B may be configured to partially inhibit movement of syringe 10 relative to housing 101 absent an application of force onto body 12 (e.g., by a user of adapter assembly 100). Accordingly, the pair of retaining elements 110A, 110B may be configured to maintain a position and/or orientation of syringe 10 relative to housing 101, such as from natural gravitational forces, but not prevent the user from applying a proximal and/or distal force onto body 12 to move syringe 10 to a desired position and/or orientation relative to adapter assembly 100.

Still referring to FIGS. 1 and 2, the user may utilize the pair of alignment mechanisms 105 as a visual reference for aligning and moving syringe 10 through housing 101. For example, syringe 10 may be moved (e.g., translated, rotated, etc.) relative to housing 101 to position the flange of syringe 10 (at proximal end 16) at a desired location and/or orientation relative to the pair of alignment mechanisms 105. In the example, the pair of alignment mechanisms 105 are spaced apart from first opening 108A such that alignment mechanisms 105 are not positioned within a travel path of body 12 (and/or the flange at proximal end 16) as syringe 10 is moved through channel 108.

In another example, one or more of the pair of alignment mechanisms 105 may be movable relative to housing 101, and particularly proximal body 102. For example, at least one alignment mechanism 105 may include a movable arm that is coupled to a hinge, such that alignment mechanism 105 may be configured to move (e.g., pivot) relative to the proximal (top) surface of proximal body 102. In this instance, the movable arm of alignment mechanism 105 may be positioned at least partially over first opening 108A such that alignment mechanism 105 may be within the travel path of body 12 as syringe 10 is moved through channel 108. The swingable arm of alignment mechanism 105 may engage a portion of body 12, such as the flange at proximal end 16, to fix a relative position and/or orientation of body 12 relative to housing 101 until the swingable arm is moved away from first opening 108A and out of the travel path of body 12. In a further example, an adapter assembly may include an alignment mechanism that is moveable (e.g., slidably) coupled to a slot on a housing of the adapter assembly, and the alignment mechanism may be movable between multiple positions in the slot to selectively block and allow movement of the flange toward first opening 108A (see, e.g., FIGS. 6-8).

Figure 4:
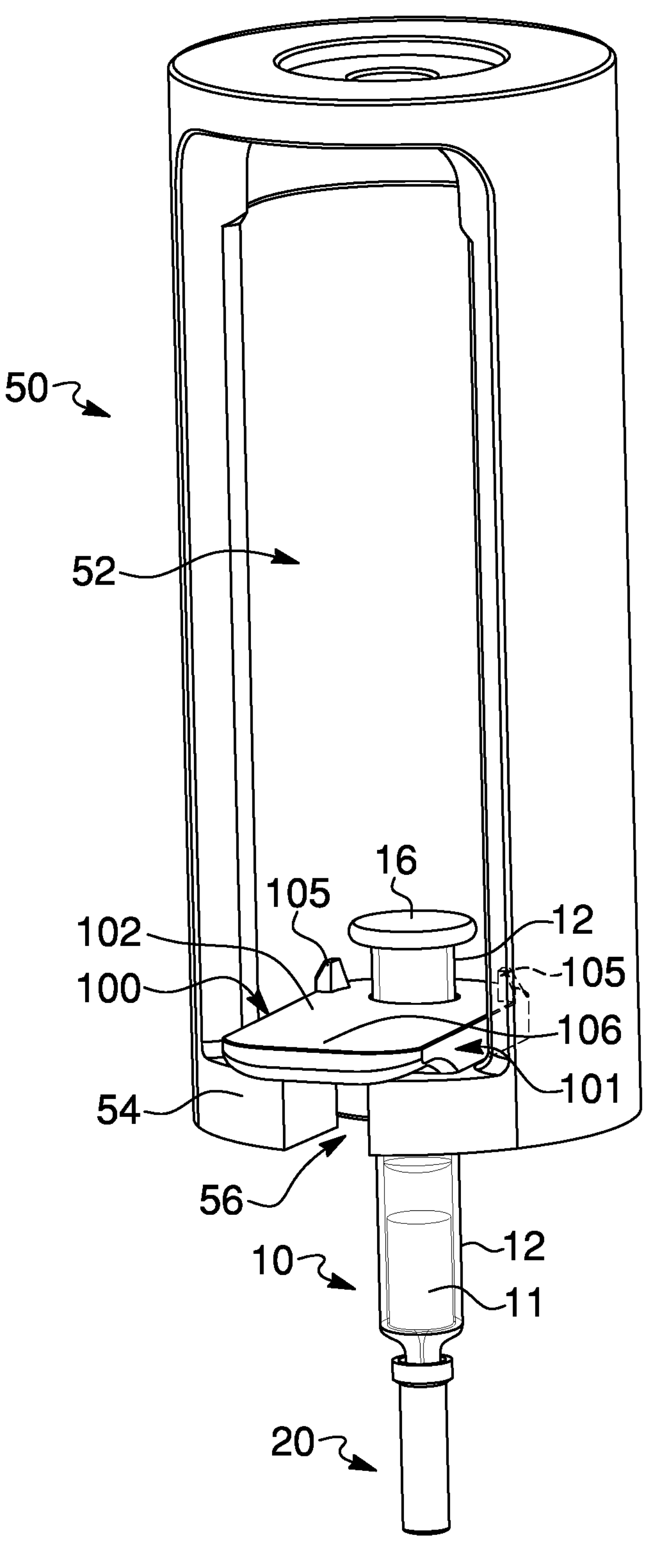
FIG. 4 depicts a perspective view of an exemplary testing instrument receiving the adapter assembly and syringe depicted in FIG. 1, according to additional aspects of the present disclosure.

Referring now to FIG. 4, the assembled syringe 10 and adapter assembly 100 (referred to herein as "the assembly") may be received within a fixture component 50 of a testing instrument. The fixture component 50 may include a cavity 52 and a bottom wall 54 that has an opening 56. With the assembly of syringe 10 and adapter assembly 100 received within cavity 52 of the fixture component 50, a portion of syringe 10 may extend through the bottom wall 54 via opening 56. The assembly may be suspended within the fixture component 50 in response to adapter assembly 100 forming a frictional engagement with one or more portions of the fixture component 50.

In other words, adapter assembly 100 may be configured to engage the fixture component 50 to securely fix syringe 10 thereto. One or more portions of housing 101 may form a friction fit with one or more surfaces of the fixture component 50. For example, at least a portion of housing 101 may be sized and/or shaped in accordance with a cross-sectional dimension of each of the cavity 52 and the opening 56 on the bottom wall 54 to form a friction fit with multiple surfaces of the fixture component 50.

Distal body 104 may be sized and/or shaped in accordance with a diameter of the opening 56, such that adapter assembly 100 may be configured to couple syringe 10 to the fixture component 50 in response to distal body 104 being received within the opening 56. Further, proximal body 102 may be sized and/or shaped greater than the diameter of the opening 56, and in accordance with a diameter of the cavity 52, such that adapter assembly 100 may be configured to couple syringe 10 to the fixture component 50 in response to proximal body 102 being received within the cavity 52. Adapter assembly 100 may be selectively decoupled from the fixture component 50 upon manually removing housing 101 from within the cavity 52 and the opening 56, such as by grasping handle 106.

Still referring to FIG. 4, handle 106 may rest against a top surface of the bottom wall 54 and a user of adapter assembly 100 may access the assembly of syringe 10 and adapter assembly 100 by grasping handle 106, such as for removing the assembly from the fixture component 50 upon completion of the testing procedures. With syringe 10 received through adapter assembly 100, syringe 10 may be securely coupled to the fixture component 50 and at least a portion of body 12 may extend outward (i.e., distally) from the fixture component 50 through the opening 56. As described herein, adapter assembly 100 may be configured to suspend syringe 10 from the fixture component 50 and relative to a testing site positioned adjacent to the fixture component 50.

Adapter assembly 100 may be configured to compensate for and/or minimize a load (e.g., a force) applied to syringe 10 (e.g., by the fixture component 50 and/or housing 101) by maintaining one or more portions of syringe 10 in a suspended position relative to the fixture component 50 and/or housing 101. For example, with first retaining element 110A and second retaining element 110B abutting against body 12 within channel 108 (see FIG. 2), adapter assembly 100 may be configured to separate the flange of syringe 10 (at proximal end 16) from one or more adjacent surfaces when the assembly of syringe 10 and adapter assembly 100 are received within the fixture component 50.

Accordingly, adapter assembly 100 may reduce the application of a pre-load onto syringe 10, such as at proximal end 16, prior to commencing testing procedures with the testing instrument by maintaining syringe 10 in a floating state in which the flange is elevated (e.g., proximally) relative to proximal body 102. By reducing undesirable loads from being applied to syringe 10 prior to testing, adapter assembly 100 may allow a user to set and/or regulate the total pre-load experienced by syringe 10 for test control purposes (e.g., as measured by a load cell of the testing instrument communicatively coupled to the fixture component 50 and/or to grips attached to clamps 58A, 58B).

Figure 5:
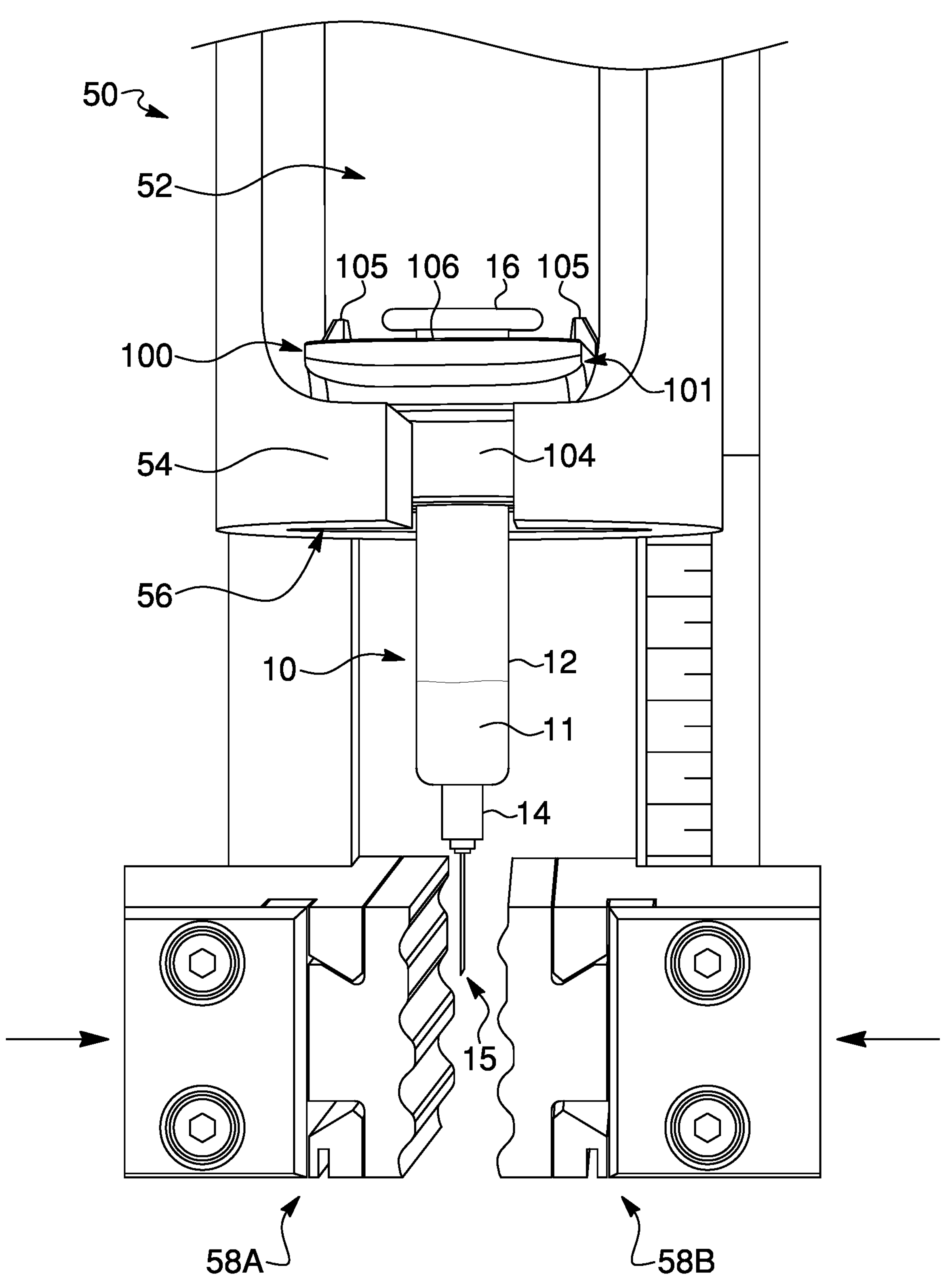
FIG. 5 depicts a side view of the testing instrument of FIG. 4, according to additional aspects of the present disclosure.

As seen in FIG. 5, with cap 20 removed from distal end 14 to expose needle 15, needle 15 may be positioned between a pair of clamps 58A, 58B of the testing instrument. Prior to administering a test sample of substance 11 from syringe 10, the pair of clamps 58A, 58B may be actuated (e.g. moved) toward needle 15 to securely engage syringe 10. In this instance, a force may be applied to syringe 10, in an axial direction that is parallel to a longitudinal length of syringe 10, from the engagement of clamps 58A, 58B with needle 15. Adapter assembly 100 may be configured to minimize an axial load endured by syringe 10 at proximal end 16 in response to the pair of clamps 58A, 58*b* engaging needle 15.

Specifically, by maintaining the flange of syringe 10 (at proximal end 16) in a suspended position relative to housing 101, adapter assembly 100 may be configured to separate the flange from one or more adjacent surfaces that may apply an inadvertent load onto syringe 10 when the pair of clamps 58A, 58B engage needle 15. First retaining element 110A and second retaining element 110B may at least partially inhibit movement (e.g. translation) of syringe 10 relative to housing 101, upon the engagement of the clamps 58A, 58B with needle 15, by abutting against an exterior of body 12 (FIG. 2). Thus, adapter assembly 100 may maintain the flange at proximal end 16 in the floated state and separated from contacting housing 101, thereby minimizing a pre-load applied to syringe 10 prior to the administration of the testing procedures.

The fixture component 50 of the testing instrument, and specifically the opening 56, may be positioned over a testing site suitable for receiving samples from syringe 10. With syringe 10 received within the fixture component 50 and suspended over the testing site by adapter assembly 100, a sample of substance 11 (stored within body 12) may be accurately administered onto the testing site, such as in response to clamps 58A, 58B removing needle 15 from syringe 10. In other embodiments, syringe 10 may be without any substance 11 stored in body 12 during the testing procedure.

Retaining elements 110A, 110B may align syringe 10, and particularly needle 15, with the testing site by abutting against body 12 at spaced intervals within channel 108 to maintain syringe 10 in a linear configuration that is parallel and/or collinear with the central longitudinal axis A of channel 108 (FIGS. 2-3). With distal body 104 received by, and centered within, the opening 56 of the bottom wall 54, the central longitudinal axis A of channel 108 may be aligned with the testing site. Accordingly, adapter assembly 100 may be configured to maintain needle 15 in parallel alignment with the testing site during test trials that involve removing needle 15 from syringe 10.

Figure 6:
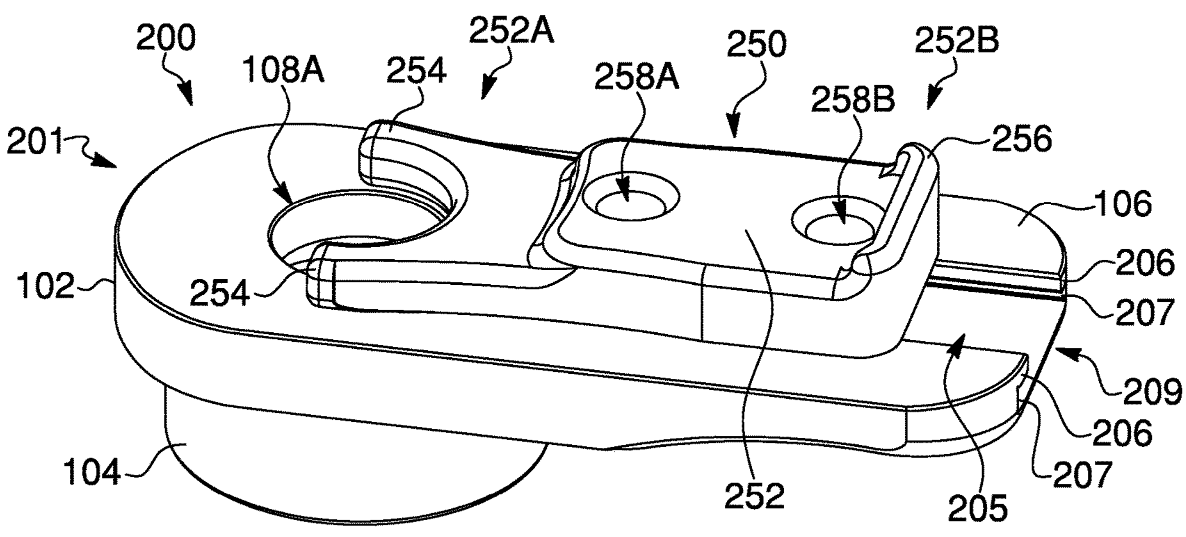
FIG. 6 depicts a perspective view of another exemplary adapter assembly in a first position, according to aspects of the present disclosure.

Referring now to FIG. 6, another exemplary adapter assembly 200 is depicted. Adapter assembly 200 may include similar structure as adapter assembly 100 shown and described above, such that like reference numerals are used to identify like components. Adapter assembly 200 may be configured and operable like adapter assembly 100 except for the differences explicitly noted herein. For example, adapter assembly 200 may include a housing 201 defined by a proximal body 102 and a distal body 104, with proximal body 102 having a greater cross-sectional profile than distal body 104. Housing 201 may include a handle 106 extending laterally outward from proximal body 102, and a slot 205 formed along a proximal (top) surface of handle 106.

Slot 205 may be recessed relative to the proximal (top) surface of handle 106, and may extend along at least a portion of a longitudinal length of housing 201. Stated differently, slot 205 may have a longitudinal length that is parallel to a longitudinal length of housing 201. For example, slot 205 may extend from a first end, positioned adjacent to proximal body 102, to a second (opposite) end positioned adjacent to handle 106. Slot 205 may be further defined by a pair of opposing sidewalls 207 and a lip 206 extending over each of the pair of opposing sidewalls 207. As depicted in the figures, slot 205 may include a substantially inverted T-shaped configuration.

A width of slot 205 may be defined by the pair of opposing sidewalls 207, and the lip 206 may extend over each sidewall 207, thereby forming a track along sidewalls 207 and underneath the overhang of lip 206. As described herein, housing 201 may be configured to receive an alignment mechanism 250 within slot 205, and the pair of opposing sidewalls 207 may be configured to interface with and guide alignment mechanism 250 to a plurality of positions along slot 205.

Still referring to FIG. 6, housing 201 may include an opening 209 at the second end of slot 205. Opening 209 may be sized and shaped to receive a portion of alignment mechanism 250, thereby facilitating receipt and/or removal of alignment mechanism 250 from within slot 205. Alignment mechanism 250 may include a movable body 252 having a longitudinal length defined between a first end 252A and a second end 252B.

Movable body 252 may include one or more legs 254 at the first end 252A, and a ledge 256 at the second end 252B. Alignment mechanism 250 may include one or more apertures along a proximal (top) surface of movable body 252 for receiving one or more securing mechanisms (e.g., fasteners). In the example shown in FIG. 6, alignment mechanism 250 includes at least a first aperture 258A and at least a second aperture 258B. As described in detail below, first aperture 258A may be configured to receive a first fastener (e.g., a screw, not shown) and second aperture 258B may be configured to receive a second fastener (e.g., a screw, not shown), and each of the fasteners may facilitate securing movable body 252 to a connector 260 of alignment mechanism 250 and/or to a fixed position relative to housing 201. Although two apertures 258A, 258B are shown in the example, alignment mechanism 250 may include additional and/or fewer apertures without departing from a scope of this disclosure. Moreover, although the figures and description describe the use of one or more fasteners to secure movable body 252 to connector 260, those of ordinary skill in the art will recognize that any suitable securing or locking mechanism may be used to couple movable body 252 to connector 260.

Still referring to FIG. 6, the first end 252A of movable body 252 may be U-shaped with a pair of legs 254 defining terminal ends of the first end 252A. The pair of legs 254 may be separated from one another by a predetermined distance, such as a distance corresponding to a diameter of first opening 108A. Alternatively, the spacing between legs 254 may be sized to correspond to an outside diameter of a syringe barrel (e.g., body 12) intended for testing. Ledge 256 may define an elevated surface at the second end 252B of movable body 252 that is raised relative to a proximal (top) surface of movable body 252. Ledge 256 may have an ergonomic profile that is configured to facilitate a user in manually grasping ledge 256 to actuate alignment mechanism 250, such as to move movable body 252 between one or more positions relative to housing 201.

Figure 7:
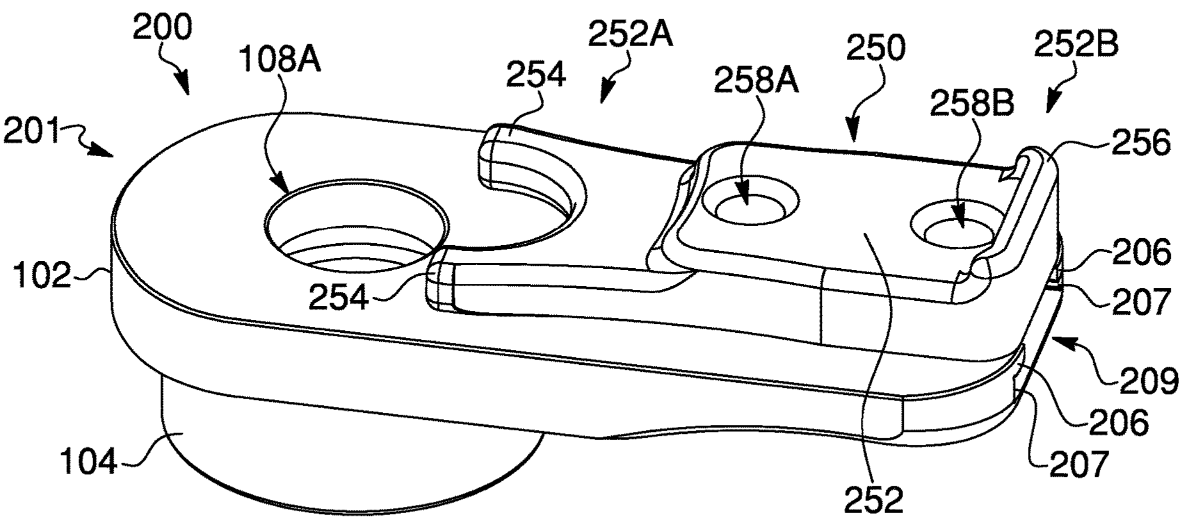
FIG. 7 depicts a perspective view of the adapter assembly of FIG. 6 in a second position, according to aspects of the present disclosure.

In some embodiments, movable body 252 may be configured to move relative to housing 201 between at least a first position, as seen in FIG. 6, and at least a second position seen in FIG. 7. In the first position, legs 254 may be positioned adjacent to first opening 108A, and positioned within a travel path of proximal end 16 as syringe 10 is received through first opening 108A. Legs 254 may be configured to engage a portion of syringe 10, such as the flange at proximal end 16, as body 12 moves distally through channel 108. Legs 254 may be sized and/or shaped to form an obstruction and/or impediment within the travel path of body 12 as syringe 10 is moved through housing 201 while alignment mechanism 250 is in the first position.

Accordingly, alignment mechanism 250 may be configured to inhibit the flange at proximal end 16 from moving distally toward proximal body 102 when legs 254 are positioned between the flange and proximal body 102. In this instance, legs 254 may provide an impediment for the flange from contacting the proximal (top) surface of proximal body 102. Accordingly, a position and/or orientation of body 12 relative to housing 201 may be fixed when alignment mechanism 250 is in the first position, Given the U-shape of the first end 252A of movable body 252 and a separation distance between legs 254, alignment mechanism 250 may still allow body 12 to be received through first opening 108A and into channel 108 as legs 254 inhibit proximal end 16 from contacting proximal body 102.

Alignment mechanism 250 may provide an aid in aligning body 12 relative to housing 201 when the pair of legs 254 are positioned adjacent to first opening 108A and blocking the flange from contacting proximal body 102. For example, in the first position seen in FIG. 6, alignment mechanism 250 may serve as a visual reference for positioning syringe 10 relative to adapter assembly 200. Additionally, alignment mechanism 250 may provide a physical stop for syringe 10, thereby providing a further reference for positioning syringe 10 relative to adapter assembly 200. A size (e.g., a height) and/or shape of legs 254 may at least partially define an allowed extent of distal movement of body 12 relative to housing 201 while alignment mechanism 250 is in the first position.

Referring now to FIG. 7, alignment mechanism 250 may be configured to move to the second position relative to housing 201. In particular, movable body 252 may translate over handle 106, through slot 205, and toward opening 209 when moving to the second position. The pair of legs 254 may be moved away from first opening 108A, thereby removing the obstruction from the travel path of body 12 and its corresponding flange. With legs 254 no longer positioned adjacent to first opening 108A, the flange at proximal end 16 may move distally toward housing 201 until encountering proximal body 102.

Although alignment mechanism 250 is shown and described herein relative to two positions, it should be appreciated that adapter assembly 200 may be configured such that alignment mechanism 250 may include additional and/or fewer positions relative to housing 201. In some embodiments, adapter assembly 200 may be configured such that alignment mechanism 250 may be removed entirely from housing 201, such as by translating movable body 252 through opening 209 and out of slot 205. Accordingly, adapter assembly 200 may be configured to decouple alignment mechanism 250 from housing 201 by moving movable body 252 out of slot 205 via opening 209. In some instances, the second position of alignment mechanism 250 may correspond to removing movable body 252 from slot 205 entirely.

Figure 8:
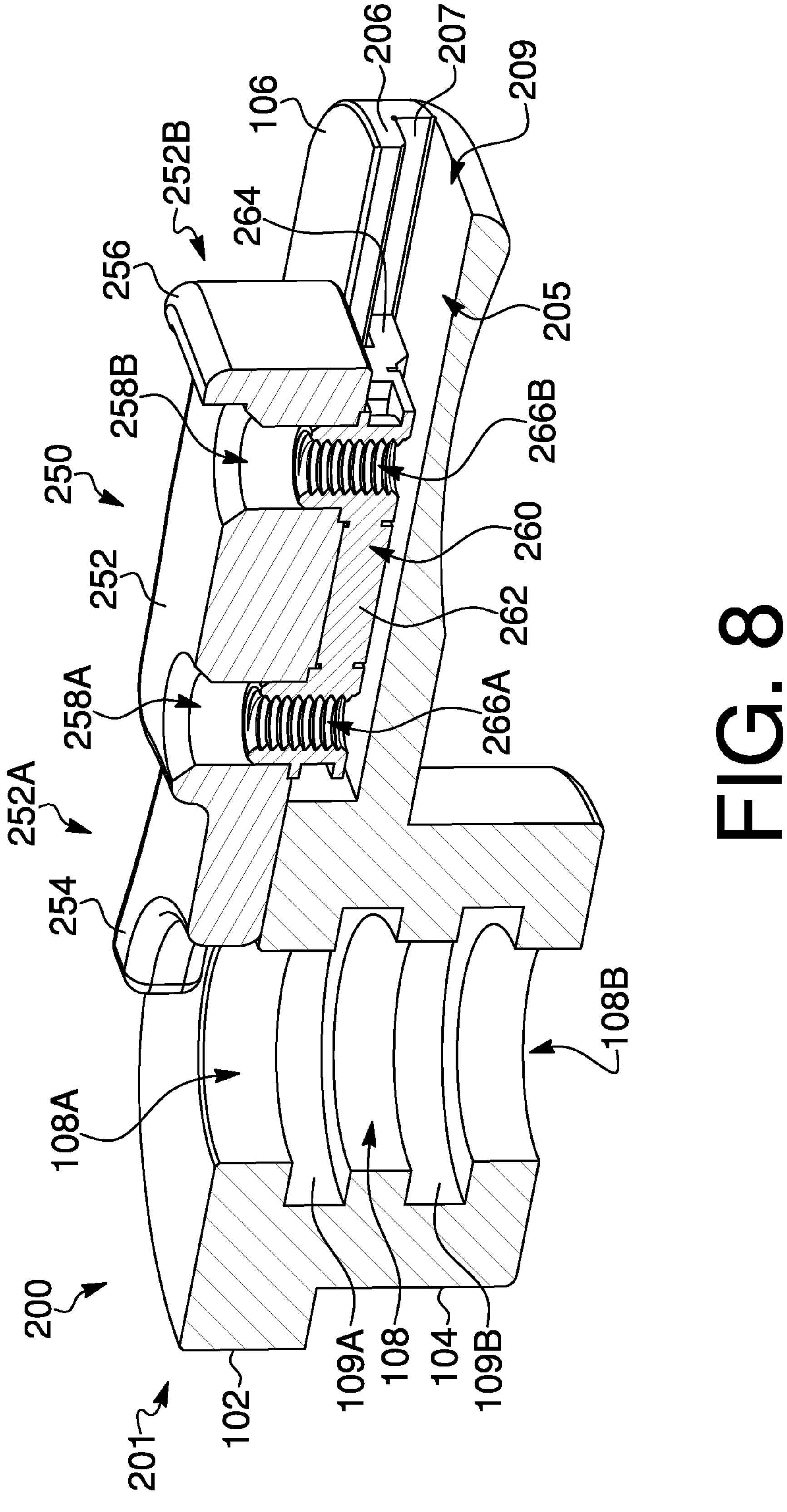
FIG. 8 depicts a cross-sectional side view of the adapter assembly of FIG. 6, according to aspects of the present disclosure.

Referring now to FIG. 8, alignment mechanism 250 may include connector 260 disposed within slot 205 and at least partially received within movable body 252, such as within first aperture 258A and second aperture 258B. Connector 260 may be positioned distally from (e.g., underneath) movable body 252, and coupled to movable body 252 along a distal (bottom) surface of movable body 252. As described herein, movable body 252 may be coupled to connector 260 by receiving a first fastener in first aperture 258A for engagement with a first threaded channel 266A of connector 260, and a second fastener in second aperture 258B for engagement with a second threaded channel 266B of connector 260. When coupled together, connector 260 may be configured to move through slot 205 in response to a corresponding movement of movable body 252 along the proximal (top) surface of housing 201. As described herein, connector 260 may interface with slot 205 and couple movable body 252 to housing 201.

In the example, connector 260 may include a linear bearing having a body 262 that is sized and shaped to be received within slot 205. Body 262 may include a pair of outer edges and/or rails 264 extending along opposing sidewalls of body 262. The pair of rails 264 may be sized and shaped in accordance with the pair of sidewalls 207 of slot 205, such that rails 264 may be received underneath the overhang defined by lip 206. As such, the pair of rails 264 may be movable along the track defined by sidewalls 207 to facilitate movement of alignment mechanism 250 through slot 205. With rails 264 received along sidewalls 207 and underneath lips 206, connector 260 may be securely coupled to slot 205, thereby connecting alignment mechanism 250 to adapter assembly 200.

Still referring to FIG. 8, connector 260 may include at least one threaded channel for each aperture on movable body 252. In the example, connector 260 may include first threaded channel 266A extending proximally outward from body 262 for receipt within first aperture 258A, such as from a proximal direction. Connector 260 may include second threaded channel 266B extending proximally outward from body 262 for receipt within second aperture 258B, such as from a proximal direction. With threaded channels 266A, 266B extending into and received within the corresponding apertures 258A, 258B, body 262 may be securely coupled to movable body 252 via one or more fasteners. Accordingly, movement (e.g., translation) of movable body 252 along an exterior surface of housing 201 may provide for a simultaneous movement of body 262 within slot 205.

First threaded channel 266A may be configured to engage with a first fastener received from first aperture 258A, and second threaded channel 266B may be configured to engage with a second fastener received from second aperture 258B, to couple body 262 to movable body 252. In one example, the fasteners may include screws that are configured to mate with the respective threaded portions of first threaded channel 266A and second threaded channel 266B. In some examples, the fasteners may be further configured to securely fix a position of alignment mechanism 250 (e.g., at one or more of the first position, the second position, etc.) relative to housing 201 by engaging slot 205 when received through the corresponding apertures 258A, 258B and threaded channels 266A, 266B.

By inserting the fasteners through the apertures 258A, 258B and mating an exterior threaded surface of the fasteners with the interior threaded surface of threaded channels 266A, 2668, a terminal (distal) end of the fasteners may translate distally through body 262 to engage a surface of slot 205. In this instance, a frictional engagement may be formed between alignment mechanism 250 and housing 201. The frictional engagement between the fasteners and slot 205 may be configured to inhibit movement of alignment mechanism 250 relative to housing 201 until the distally-directed force applied to slot 205 by the fasteners is minimized and/or removed.

Features enumerated above have been described within the context of particular embodiments and/or examples. However, as one of ordinary skill in the art would understand, features and aspects of each embodiment or example may be combined, added to other embodiments or examples, subtracted from an embodiment, etc. in any manner suitable to assist with controlled preparation and/or delivery of a drug. While a number of embodiments and/or examples are presented herein, multiple variations on such embodiments, and combinations of elements from one or more embodiments, are possible and are contemplated to be within the scope of the present disclosure. Moreover, those skilled in the art will appreciate that the conception upon which this disclosure is based may readily be used as a basis for designing other devices, methods, and systems for carrying out the several purposes of the present disclosure.

The present disclosure is further described by the following non-limiting items:

Item 1. An adapter assembly, comprising:

a housing including:

- a channel formed within the housing, and configured to receive a medical device;
- a first groove formed along an interior wall of the channel, and configured to at least partially receive a first retaining element; and
- a second groove formed along the interior wall of the channel, and configured to at least partially receive a second retaining element;

wherein the first retaining element is configured to extend outward from the first groove and the second retaining element is configured to extend outward from the second groove, such that each of the first retaining element and the second retaining element abuts against a body of the medical device that is received through the channel.

Item 2. The adapter assembly of item 1, wherein the first retaining element and the second retaining element are configured to align the body of the medical device relative to a central longitudinal axis of the channel.

Item 3. The adapter assembly of item 1, wherein the first retaining element and the second retaining element are configured to maintain the body of the medical device in a suspended position relative to the housing.

Item 4. The adapter assembly of item 3, wherein the first retaining element and the second retaining element are configured to offset a proximal end of the body from a proximal surface of the housing when the medical device is in the suspended position.

Item 5. The adapter assembly of item 4, wherein the first retaining element and the second retaining element are configured to minimize a load applied to the medical device by the housing when separating the proximal end of the body from the proximal surface of the housing.

Item 6. The adapter assembly of item 4, further comprising an alignment mechanism positioned on a proximal surface of the housing, the alignment mechanism is configured to position the proximal end of the medical device relative to the housing.

Item 7. The adapter assembly of item 6, wherein the housing includes a slot on the proximal surface, the slot being configured to slidably receive the alignment mechanism between a plurality of positions within the slot.

Item 8. The adapter assembly of item 7, wherein the alignment mechanism is movable between a first position and a second position relative to the slot; wherein in the first position, the alignment mechanism is configured to limit movement of the proximal end of the medical device relative to the housing, and in the second position, the alignment mechanism is configured to allow movement of the proximal end of the medical device relative to the housing.

Item 9. The adapter assembly of item 1, wherein the housing includes a handle configured to removably couple the adapter assembly to a testing instrument, and the medical device includes a syringe having a needle.

Item 10. The adapter assembly of item 9, wherein the adapter assembly is configured to align the needle relative to the testing instrument when the syringe is received in the housing and the adapter assembly is coupled to the testing instrument.

Item 11. The adapter assembly of item 9, wherein the adapter assembly is configured to suspend the syringe within the testing instrument such that the body of the syringe is separated from one or more surfaces of the testing instrument.

Item 12. The adapter assembly of item 11, wherein the first retaining element and the second retaining element are configured to minimize a load applied to the syringe by the testing instrument by separating a proximal flange of the syringe from the housing and the one or more surfaces of the testing instrument.

Item 13. The adapter assembly of item 1, wherein a cross-sectional dimension of each of the channel, the first retaining element, and the second retaining element define a grip diameter of the adapter assembly, the grip diameter of the adapter assembly varies along a longitudinal length of the housing.

Item 14. The adapter assembly of item 1, wherein each of the first retaining element and the second retaining element are formed of an elastomeric material that is flexibly deformable.

Item 15. An adapter assembly, comprising:

a housing including:

a channel configured to receive a portion of a medical device;

a pair of grooves formed along an interior wall of the channel, wherein each of the pair of grooves are longitudinally offset from one another along the interior wall; and a pair of retaining elements, wherein each of the pair of retaining elements is at least partially received within at least one of the pair of grooves; and wherein the pair of retaining elements is configured to extend outward from the pair of grooves and into the channel, thereby interfacing with the portion of the medical device received through the channel.

Item 16. The adapter assembly of item 15, wherein the housing includes an alignment mechanism and a slot formed along a proximal surface of the housing, the alignment mechanism is configured to move through the slot to a plurality of positions relative to the proximal surface of the housing.

Item 17. The adapter assembly of item 16, wherein, in a first position of the alignment mechanism relative to the slot, the alignment mechanism is configured to engage a portion of the medical device, thereby obstructing movement of the medical device relative to the adapter assembly; and wherein, in a second position of the alignment mechanism relative to the slot, the alignment mechanism is configured to disengage the portion of the medical device, thereby permitting movement of the medical device relative to the adapter assembly.

Item 18. The adapter assembly of item 16, wherein the alignment mechanism includes a movable body and a connector coupled to the movable body, the movable body has a pair of apertures that are each configured to receive a securing mechanism for coupling the movable body to the connector.

Item 19. The adapter assembly of item 18, wherein the movable body is disposed over the proximal surface of the housing and the connector is disposed within the slot; wherein the alignment mechanism is configured such that movement of the movable body relative to the proximal surface causes a corresponding movement of the connector through the slot.

Item 20. A method for holding a medical device with an adapter assembly, comprising: inserting the medical device through a channel of the adapter assembly, the channel including a pair of grooves separated from one another along a longitudinal length of the channel and at least one retaining element received within each of the pair of grooves for suspending the medical device inside the channel; positioning an alignment mechanism of the adapter assembly in a first position to impede movement of the medical device relative to the channel by engaging a portion of the medical device; and positioning the alignment mechanism of the adapter assembly in a second position to allow movement of the medical device relative to the channel by disengaging the portion of the medical device.

What is claimed is:

1. An adapter assembly, comprising:

a housing including:

a channel formed within the housing, and configured to receive a medical device;

a first groove formed along an interior wall of the channel, and configured to at least partially contain a first retaining element fixed relative to the interior wall; and a second groove formed along the interior wall of the channel, and configured to at least partially contain a second retaining element fixed relative to the interior wall;

wherein each of the first groove and the second groove extends circumferentially about the interior wall of the channel;

wherein the first retaining element is configured to extend outward from the first groove and the second retaining element is configured to extend outward from the second groove, such that each of the first retaining element and the second retaining element abuts against a barrel of the medical device that is received through the channel; and wherein each of the first retaining element and the second retaining element is configured to compress radially-outward from a central longitudinal axis of the channel while remaining longitudinally fixed relative to the interior wall when the barrel of the medical device is received through the channel, and the housing is configured to enable the barrel to extend through the channel such that a portion of the barrel extends outward from at least one opening of the housing.

2. The adapter assembly of claim 1, wherein the first retaining element and the second retaining element are configured to align the barrel of the medical device relative to the central longitudinal axis of the channel.

3. The adapter assembly of claim 1, wherein the first retaining element and the second retaining element are configured to maintain the barrel of the medical device in a suspended position relative to the housing and permit movement of the medical device relative to the first retaining element and the second retaining element as the medical device is received through the channel.

4. The adapter assembly of claim 3, wherein the first retaining element and the second retaining element are configured to offset a proximal end of the barrel from a proximal surface of the housing when the medical device is in the suspended position.

5. The adapter assembly of claim 4, wherein the first retaining element and the second retaining element are configured to minimize a load applied to the medical device by the housing when separating the proximal end of the barrel from the proximal surface of the housing.

6. The adapter assembly of claim 4, further comprising an alignment mechanism positioned on the proximal surface of the housing, the alignment mechanism is configured to position the proximal end of the medical device relative to the housing.

7. The adapter assembly of claim 6, wherein the housing includes a slot on the proximal surface, the slot being configured to slidably receive the alignment mechanism between a plurality of positions within the slot.

8. The adapter assembly of claim 7, wherein the alignment mechanism is movable between a first position and a second position relative to the slot;

wherein in the first position, the alignment mechanism is configured to limit movement of the proximal end of the medical device relative to the housing, and in the second position, the alignment mechanism is configured to allow movement of the proximal end of the medical device relative to the housing.

9. The adapter assembly of claim 1, wherein the housing includes a handle configured to removably couple the adapter assembly to a testing instrument, and the medical device includes a syringe having a needle.

10. The adapter assembly of claim 9, wherein the adapter assembly is configured to align the needle relative to the testing instrument when the syringe is received in the housing and the adapter assembly is coupled to the testing instrument.

11. The adapter assembly of claim 9, wherein the adapter assembly is configured to suspend the syringe within the testing instrument such that the barrel of the syringe is separated from one or more surfaces of the testing instrument.

12. The adapter assembly of claim 11, wherein the first retaining element and the second retaining element are configured to minimize a load applied to the syringe by the testing instrument by separating a proximal flange of the syringe from the housing and the one or more surfaces of the testing instrument.

13. The adapter assembly of claim 1, wherein a cross-sectional dimension of each of the channel, the first retaining element, and the second retaining element define a grip diameter of the adapter assembly, the grip diameter of the adapter assembly varies along a longitudinal length of the housing.

14. The adapter assembly of claim 1, wherein each of the first retaining element and the second retaining element are formed of an elastomeric material that is flexibly deformable.

15. An adapter assembly, comprising:

a housing including:

a channel configured to receive a barrel of a medical device;

a pair of grooves formed along an interior wall of the channel, wherein each of the pair of grooves is longitudinally offset from one another along the interior wall; and a pair of retaining elements, wherein each of the pair of retaining elements is at least partially contained within at least one of the pair of grooves and fixed relative to the interior wall; and wherein each of the pair of grooves extends circumferentially about the interior wall of the channel;

wherein each of the pair of retaining elements is configured to extend outward from the pair of grooves and into the channel, thereby interfacing with a first portion of the barrel of the medical device received through the channel;

wherein each of the pair of retaining elements is configured to compress into the pair of grooves and out of the channel while remaining longitudinally fixed relative to the interior wall when the first portion of the barrel of the medical device is received through the channel; and wherein the housing is configured to enable the barrel of the medical device to extend through the channel such that a second portion of the barrel of the medical device extends outward from at least one opening of the housing.

16. The adapter assembly of claim 15, wherein the housing includes an alignment mechanism and a slot formed along a proximal surface of the housing, the alignment mechanism is configured to move through the slot to a plurality of positions relative to the proximal surface of the housing.

17. The adapter assembly of claim 16, wherein, in a first position of the alignment mechanism relative to the slot, the alignment mechanism is configured to engage a portion of the medical device, thereby obstructing movement of the medical device relative to the adapter assembly; and wherein, in a second position of the alignment mechanism relative to the slot, the alignment mechanism is configured to disengage the portion of the medical device, thereby permitting movement of the medical device relative to the adapter assembly.

18. The adapter assembly of claim 16, wherein the alignment mechanism includes a movable body and a connector coupled to the movable body, the movable body has a pair of apertures that are each configured to receive a securing mechanism for coupling the movable body to the connector.

19. The adapter assembly of claim 18, wherein the movable body is disposed over the proximal surface of the housing and the connector is disposed within the slot;

wherein the alignment mechanism is configured such that movement of the movable body relative to the proximal surface causes a corresponding movement of the connector through the slot.

20. A method for holding a medical device with an adapter assembly, comprising:

inserting the medical device through a channel of the adapter assembly, the channel including a pair of grooves separated from one another along a longitudinal length of the channel and at least one retaining element contained within each of the pair of grooves and fixed relative to the channel for suspending the medical device inside the channel, wherein each of the pair of grooves extends circumferentially about an interior wall of the channel and the at least one retaining element is configured to compress radially-outward away from the channel and remain longitudinally fixed relative to the interior wall when the medical device is received through the channel wherein the adapter assembly is configured to enable a barrel of the medical device to extend through the channel such that the barrel extends outward from the adapter assembly;

positioning an alignment mechanism of the adapter assembly in a first position to impede movement of the medical device relative to the channel by engaging a portion of the medical device; and positioning the alignment mechanism of the adapter assembly in a second position to allow movement of the medical device relative to the channel by disengaging the portion of the medical device.

* * * * *